US009158084B2

(12) United States Patent
    Heitel (10) Patent No.: US 9,158,084 B2
(45) Date of Patent: Oct. 13, 2015

(54) SCANNING LENS SYSTEMS AND METHODS OF REDUCING REACTION FORCES THEREIN

(71) Applicant: AMO Development, LLC, Santa Ana, CA (US)

(72) Inventor: Robert G Heitel, Laguna Beach, CA (US)

(73) Assignee: AMO Development, LLC, Santa Ana, CA (US)

( * ) Notice: Subject to any disclaimer, the term of this patent is extended or adjusted under 35 U.S.C. 154(b) by 222 days.

(21) Appl. No.: 13/659,003

(22) Filed: Oct. 24, 2012

(65) Prior Publication Data

US 2014/0114294 A1    Apr. 24, 2014

(51) Int. Cl.
| G02B 27/64 | (2006.01) |
| G02B 7/02  | (2006.01) |
| A61F 9/008 | (2006.01) |
| G02B 26/08 | (2006.01) |

(52) U.S. Cl.
    CPC .............. *G02B 7/02* (2013.01); *A61F 9/00802* (2013.01); *G02B 27/644* (2013.01); *G02B 27/648* (2013.01); *A61F 2009/00872* (2013.01); *A61F 2009/00897* (2013.01); *G02B 26/08* (2013.01)

(58) Field of Classification Search
    None
    See application file for complete search history.

(56) References Cited

U.S. PATENT DOCUMENTS

| 5,144,630 A   | 9/1992   | Lin |
| 5,646,791 A   | 7/1997   | Glockler |
| 5,683,379 A   | 11/1997  | Hohla |
| 5,713,892 A   | 2/1998   | Shimmick |
| 5,731,896 A * | 3/1998   | Baumann et al. ............. 359/557 |
| 5,742,626 A   | 4/1998   | Mead et al. |
| 5,912,775 A   | 6/1999   | Glockler |
| 6,203,539 B1  | 3/2001   | Shimmick et al. |
| 6,331,177 B1  | 12/2001  | Munnerlyn et al. |
| 6,347,549 B1  | 2/2002   | Ryan et al. |
| 7,423,787 B2* | 9/2008   | Nakajima ..................... 358/483 |
| 2003/0222143 A1* | 12/2003 | Mitchell ....................... 235/454 |
| 2006/0165397 A1* | 7/2006  | Uehara et al. ................... 396/55 |
| 2007/0030462 A1 | 2/2007  | Yuan et al. |

(Continued)

FOREIGN PATENT DOCUMENTS

| EP | 0628298 A1   | 12/1994 |
| WO | WO9418883 A1 | 9/1994  |

OTHER PUBLICATIONS

International Search Report and Written Opinion for Application No. PCT/US2013/066668, mailed on Jan. 17, 2014, 13 pages.

*Primary Examiner* — Tran Nguyen
(74) *Attorney, Agent, or Firm* — Abbott Medical Optics Inc.

(57) ABSTRACT

A scanning lens component includes a primary and transverse axis stages and motors. The primary axis motor includes a first coil moving along the primary axis in the first direction along with the primary axis stage and a first magnet configured to move in a second, opposite direction, in response to movement of the first coil a first distance that exceeds a threshold primary axis distance. The transverse axis stage is adjacent and coupled to the primary axis stage and moves along a transverse axis in a third direction. The transverse axis motor includes a second coil for moving along the transverse axis in the third direction with the transverse axis stage, and a second magnet configured to move in a fourth, opposite direction, in response to movement of the second coil along the transverse axis in the third direction a second distance that exceeds a threshold transverse axis distance.

22 Claims, 7 Drawing Sheets

(56) References Cited

U.S. PATENT DOCUMENTS

| | | | |
|---|---|---|---|
| 2007/0133092 A1* | 6/2007 | Maeda et al. | 359/557 |
| 2009/0275929 A1 | 11/2009 | Zickler | |
| 2010/0073750 A1* | 3/2010 | Yamaguchi et al. | 359/200.7 |
| 2010/0266313 A1* | 10/2010 | Nakajima | 399/151 |
| 2011/0109946 A1 | 5/2011 | Osipchuk | |

* cited by examiner

SCANNING LENS SYSTEMS AND METHODS OF REDUCING REACTION FORCES THEREIN

BACKGROUND OF THE INVENTION

1. Field of the Invention

The present invention relates in general to an ophthalmic laser system, and means to greatly reduce reaction forces in linear or curvilinear stages of the ophthalmic laser system.

2. Description of Related Art

Laser beam delivery systems are used to perform laser vision correction (LVC) procedures, such as PRK or LASIK procedures. Typically, the laser beam delivery system provides a laser beam from a pulsed laser and directs and/or focuses the laser beam at an ablation plane in which the cornea of a patient is located with precision. The laser beam delivery system conditions the beam and scans the beam across the corneal surface in order to ablate small portions of the cornea in a very controlled manner.

Because precision is required in performing LVC procedures, proper alignment is a significant concern. In particular, the laser should be properly aligned to the ablation plane, and the delivery system should be aligned to direct portions of the beam into monitoring equipment used during the procedure. As laser beam delivery systems generally are relatively complex and many systems include numerous moving parts, the slightest movement of certain system components can affect alignment. Realignment of the system components can be relatively difficult and/or time consuming to perform. However, such repositioning is necessary, as misalignment of the beam degrades the quality of the beam over time and/or damages optical components within the system and/or laser cavity (e.g., the laser output coupler).

SUMMARY OF THE INVENTION

Accordingly, there is a need for a laser beam delivery system that substantially simplifies, reduces, or eliminates the need for re-alignment of system components. In an embodiment, by way of example only, a scanning lens component for a laser beam delivery system is improved so as to reduce movement of components thereof. The scanning lens component includes a primary axis stage and motor and a transverse axis stage and motor. The primary axis stage is configured to move linearly along a primary axis in a first direction and includes a first central opening for receiving an incident beam of light. The primary axis motor is coupled to the primary axis stage and includes a first coil and a first magnet. The first coil is configured to move along the primary axis in the first direction along with the primary axis stage, and the first magnet is configured to move in a second direction opposite the first direction, in response to movement of the first coil along the primary axis in the first direction a first distance that exceeds a threshold primary axis distance. The transverse axis stage is adjacent and coupled to the primary axis stage and includes a second central opening substantially aligned with the first central opening. The transverse axis stage is configured to move at least linearly along a transverse axis in a third direction, and the transverse axis is transverse relative to the primary axis. The transverse axis motor is coupled to the transverse axis stage and including a second coil and a second magnet. The second coil is configured to move along the transverse axis in the third direction along with the transverse axis stage, and the second magnet is configured to move in a fourth direction opposite the third direction, in response to movement of the second coil along the transverse axis in the third direction a second distance that exceeds a threshold transverse axis distance.

BRIEF DESCRIPTION OF THE DRAWINGS

In order that the advantages of the invention will be readily understood, a more particular description of the invention briefly described above will be rendered by reference to specific embodiments that are illustrated in the appended drawings. Understanding that these drawings depict only typical embodiments of the invention and are not therefore to be considered to be limiting of its scope, the invention will be described and explained with additional specificity and detail through the use of the accompanying drawings, in which.

DETAILED DESCRIPTION OF THE DRAWINGS

The illustrated embodiments below provide means for greatly reducing reaction forces transmitted to a scanning lens or lens stage mounted on a laser beam delivery system. The lens stage, generally mounted to an arm extending from the laser beam delivery system, includes a central opening for receiving an incident beam of light from the laser beam delivery system. The incident beam of light is directed through the central opening, toward a lens, and to a reflector. The reflector aims the incident beam of light to a desired location, such as at a cornea of an eye for laser surgery.

To minimize movement of the lens stage, in particular, in the event external forces are exerted on the lens stage, voice coil mechanisms operating as servo motors are included to counteract the external forces. In an embodiment, the lens stage is coupled to two stages, namely, a primary axis stage and an adjacent transverse axis stage, each having openings that align with each other to define the central opening and each being coupled to respective motors. The primary axis stage is capable of traveling in both directions along a primary axis, which in an embodiment is generally perpendicular to the axis of the incident beam of light. The transverse axis stage is capable of traveling in both directions along a transverse axis, which is angled, for example, substantially orthogonal, relative to the primary axis and the incident beam of light.

The primary axis motor includes a coil coupled to the primary axis stage and a cylindrical magnet. The coil is configured to move along the primary axis along with the primary axis stage, and the magnet is configured to move opposite the direction in which the coil and primary axis stage travel, in response to movement of the coil along the primary axis when the movement causes the coil to travel a first distance that exceeds a threshold primary axis distance. A transverse axis motor includes a coil coupled to the transverse axis stage and a magnet surrounding the coil. The coil is configured to move along the transverse axis along with the transverse axis stage, and the magnet is configured to move in a direction opposite the direction in which the coil and transverse axis stage are traveling, in response to movement of the coil along the transverse axis, if a distance traveled by the coil exceeds a threshold transverse axis distance.

By coupling voice coil motors with each stage, the floating magnets of each travel in response to movement of corresponding coils, to thereby counteract or cancel the movement of the coils. As a result, the stages remain stationary to hold the lens at a desired position. The new lens stage can be implemented with laser delivery systems of various configurations.

Figure 1:
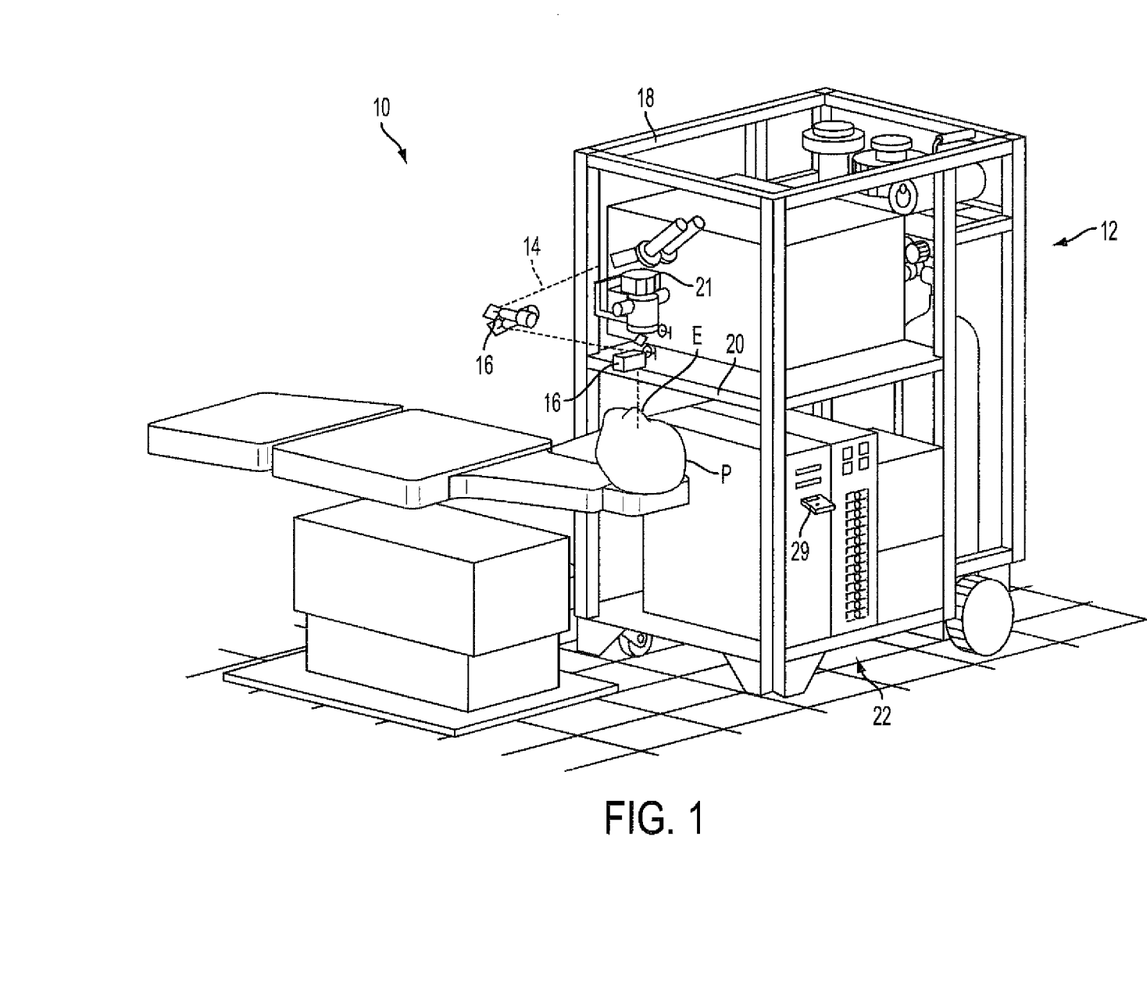
FIG. 1 is a perspective view of a laser ablation system.

FIG. 1 is a perspective view of a laser ablation system 10 in which a lens stage 11 may be implemented. Laser ablation system 10 includes a laser 12 that produces a laser beam 14. Laser delivery optics 16 are in a path of laser beam 14. Delivery optics 16 direct laser beam 14 to an eye of a patient P. A delivery optics support structure (not shown here for clarity) extends from a frame 18 supporting laser 12. An input device 20 is used to align laser system 10 in relation to the eye of a patient P. A microscope 21 is mounted on the delivery optics support structure, the microscope often being used to image a cornea of an eye. In some embodiments, a laser eye surgery system 10 includes at least some portions of an excimer laser system, such as the STAR S4 IR® Excimer Laser System available from Abbott Medical Optics Inc., Milpitas, Calif.

Laser 12 generally comprises an excimer laser and ideally comprises an argon-fluoride laser producing pulses of laser light having a wavelength of approximately 193 nm. A pulse of laser light typically has a fixed pulse duration having a full width half maximum (FWHM) of about 15 nanoseconds during a treatment. Laser 12 is preferably designed to provide a feedback stabilized fluence at the patient's eye, delivered via delivery optics 16. The present invention may also be useful with alternative sources of electromagnetic radiation, particularly those adapted to controllably ablate a corneal tissue without causing significant damage to adjacent and/or underlying tissues of the eye. The laser system may include, but is not limited to, excimer lasers such as argon-fluoride excimer lasers (producing laser energy with a wavelength of about 193 nm), solid state lasers, including frequency multiplied solid state lasers such as flash-lamp and diode pumped solid state lasers. Exemplary solid state lasers include UV solid state lasers (approximately 193-215 nm) such as those described in U.S. Pat. Nos. 5,144,630 and 5,742,626. Laser energy may comprise a beam formed as a series of discreet laser pulses. A variety of alternative lasers might also be used. Hence, although an excimer laser is the illustrative source of an ablating beam, other lasers may be used in the present invention.

Laser 12 and delivery optics 16 generally direct laser beam 14 to the eye of patient P under direction of a processor 22. For example, processor 22 selectively adjusts laser beam 14 to expose portions of the cornea to pulses of laser energy so as to effect a predetermined sculpting of a cornea and alter refractive characteristics of an eye. In many embodiments, both laser 14 and a laser delivery optical system 16 will be under computer control of processor 22 to effect a desired laser sculpting process, with processor 22 effecting (and optionally modifying) a pattern of laser pulses. Processor 22 may comprise (or interface with) a conventional PC system including standard user interface devices such as a keyboard, a display monitor, and the like. Processor 22 will typically include an input device such as a magnetic or optical disk drive, an internet connection, or the like.

The pattern of pulses may by summarized in a treatment table listing of machine readable data of a tangible storage media 29 and may be adjusted according to feedback input into processor 22 from an automated image analysis system (manually input into processor 22 by a system operator) in response to feedback data provided from an ablation monitoring system feedback system. Tangible storage media 29 may comprise a floppy disk, an optical disk, a data tape, a volatile or non-volatile memory, or the like, and a processor 22 will include memory boards and other standard components of modern computer systems for storing and executing a computer program code. Tangible storage media 29 may optionally embody wavefront sensor data, wavefront gradients, a wavefront elevation map, a treatment map, a corneal topography map, a measurement of a refraction of an eye, an ablation table, and/or instructions to adjust the amount of energy. Feedback might be provided by integrating a wavefront measurement system described below with a laser treatment system 10, and processor 22 may continue and/or terminate a sculpting treatment in response to feedback, and may optionally also modify a planned sculpting based at least in part on feedback.

Laser beam 14 may be adjusted to produce a desired sculpting using a variety of alternative mechanisms and may be selectively limited using one or more variable apertures. An exemplary variable aperture system having a variable iris and a variable width slit is described in U.S. Pat. No. 5,713,892, the full disclosure of which is incorporated herein by reference. A laser beam may also be tailored by varying a size and offset of a laser spot from an axis of an eye, as described in U.S. Pat. No. 5,683,379, and as also described in co-pending U.S. patent application Ser. No. 08/968,380, filed Nov. 12, 1997; and Ser. No. 09/274,999 filed Mar. 22, 1999, the full disclosures of which are incorporated herein by reference. As will be appreciated by those with skill in the art, still further computer programming and control methodologies for these laser pattern tailoring techniques are possible. Moreover, additional components and subsystems may be included with laser system 10, as should be understood by those of skill in the art.

Figure 2:
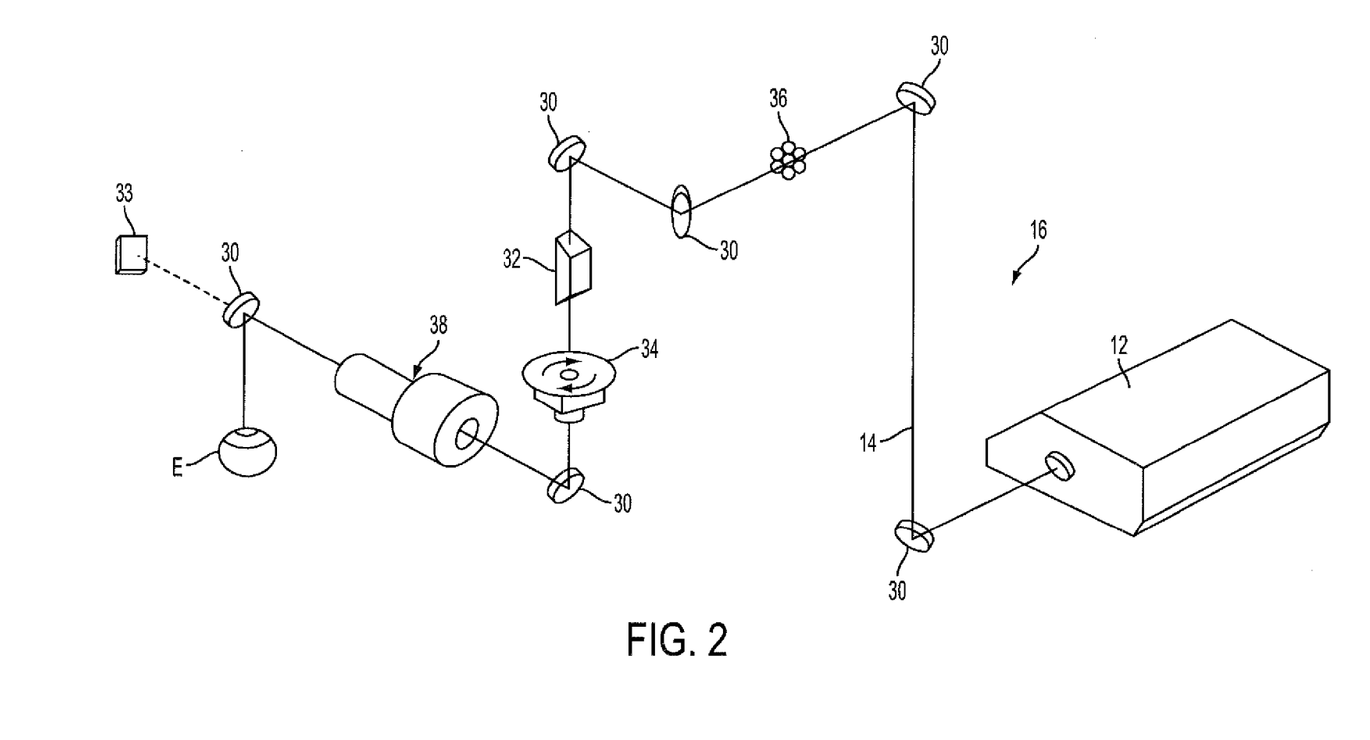
FIG. 2 is a schematic view of a simplified laser beam delivery system for selectively directing a laser beam onto corneal tissue.

Referring now to FIG. 2, laser beam delivery system 16 for directing laser beam 14 at an eye E includes a number of minors 30, as well as one or more temporal integrators 32 which may adjust (or otherwise tailor) an energy distribution across a laser beam. In an exemplary embodiment, a variable aperture 34 changes a diameter and/or slit width to profile laser beam 14, ideally including both a variable diameter iris and a variable width slit. A prism 36 separates laser beam 14 into a plurality of beamlets, which may partially overlap on eye E to smooth edges of an ablation or "crater" formed from each pulse of a laser beam. An offset module 38 includes motors which vary an angular offset of an offset lens, and which also change a radial orientation of an offset. Hence, offset module 38 can selectively direct laser beam 14 at a desired lateral region of a cornea. A structure and method for using a laser beam delivery system 16 and an offset module 38 are more fully described in U.S. Pat. Nos. 6,331,177; 6,203, 539; 5,912,775; and 5,646,791 the full disclosures of which are incorporated herein by reference. In some embodiments, laser beam delivery system 16 includes a delivered energy measurement device 33 for measuring the amount of laser beam energy delivered to the eye E.

The "delivery path" of laser beam 14 is depicted in FIG. 2 by the line labeled as laser beam 14 and is referred to generally in this application as any path along which a laser beam may travel from a laser beam generating device to a target. Thus, the present invention is not limited to any particular form of delivery path. To ensure that the delivery path is largely undisturbed during laser surgery, laser ablation system 10 includes reaction force reduction means to counteract external forces that may be imparted on to delivery optics 16. In particular, offset module 38 of delivery optics 16 includes voice coils and position sensors that together operate as servo motors to control positioning of a lens stage or scanning lens component included in delivery optics 16.

FIGS. 3-6 are various views of a scanning lens component 40 for use in offset module 38 of laser beam delivery optics system 16 of FIG. 2. Scanning lens component 40 is coupled to a support mount 42 for attaching component 40 to an arm (not shown) extending from laser 12. Scanning lens component 40 receives laser beam 14 from laser 12 and includes a lens 43 for focusing and directing laser beam 14 to mirror 30. Lens 43 is coupled to a two-axis lens stage (made up of a primary axis stage 44 and a transverse axis stage 46), which supports and maintains lens 43 when in a stationary position and directs the scanning movement of laser beam 14 (e.g., in two-axes or dimensions, such as x-direction and y-direction). Stages 44, 46 are generally planar and stacked side by side with each other. Additionally, stages 44, 46 are arranged substantially perpendicular relative to an axis along which laser beam 14 travels and each has an opening 48, 50 defining a portion of a central opening for receiving the incident beam of light (e.g., laser beam 14).

Primary axis stage 44 is arranged so that a primary axis 52 extending through the axis along which laser beam 14 travels is substantially perpendicular thereto. A linear bearing stage 54 is coupled to primary axis stage 44 to allow linear movement along primary axis 52 in a first direction 56 and a second direction 58. In an embodiment, linear bearing stage 54 includes annular ring sets 60, 62 each disposed in respective annular grooves 64, 66 formed in support mount 42 and an outer diameter 68 of primary axis stage 44. Alternatively, one or both of annular ring sets 60, 62 is replaced with ball bearings or other types of bearings.

A primary axis motor 70 is coupled to primary axis stage 44 and is configured to limit movement of primary axis stage 44 along primary axis 52. In an embodiment, primary axis motor 70 is a voice coil motor and includes a coil 72 and a magnet assembly 74 disposed at least partially within a housing 75. Coil 72 includes a tubular coil winding 76 wound around a cylindrical portion 78 of a coil holder 80. Coil holder 80 has a base 82 attached directly to primary axis stage 44, for example, along a transverse edge 84 thereof, via fasteners 86. Magnet assembly 74 includes a solid cylindrical section 88 and a tubular section 90 surrounding cylindrical section 88, each extending from a cover 92. An inner surface of tubular section 90 includes a magnetic material and is connected to a power source to selectively provide a magnetic field in magnet assembly 74. A remainder of tubular section 90 and surrounding cylindrical section 88 are formed from a soft iron core or other suitable non-magnetizable material.

Primary axis motor 70 receives positioning data from a position sensor 94 coupled to primary axis stage 44 to determine if movement of primary axis stage 44 is outside of an acceptable range or if a distance traveled by primary axis stage 44 exceeds a predetermined threshold distance. Position sensor 94 can include an optical, capacitive, inductive, other type of linear encoder or another type of sensor capable of noting exact positioning of primary axis stage 44 relative to a reference.

In an embodiment, a counterbalance spring (the location of which is generally indicated by reference number 102) is included to normalize positioning of magnet assembly 74 due to the influence of gravitational forces thereon. More particularly, counterbalance spring 102 is selected for a particular spring constant and includes an end coupled to magnet assembly 74, such to tubular section 90, and an opposite end coupled to one end of a pin 104 attached to housing 75. Pin 104 resides in a channel (not shown) formed in housing 75 and is configured to have an exposed head to allow one to tune positioning of magnet assembly 74. For instance, pin 104 can be adjusted via head to move spring axially through channel and thereby move magnet assembly 74 relative to housing 75. Inclusion of counterbalance spring 102 is useful for providing a bias force to counteract the effects of gravitational forces on magnet assembly 74.

As noted briefly above, transverse axis stage 46 is disposed between primary axis stage 44 and lens 43. More specifically, transverse axis stage 46 has an interior-facing surface 110 adjacent primary axis stage 44 and an outer-facing surface 112 from which a lens stage 114 extends. Lens stage 114 supports lens 43 and has a connector 118 extending axially therefrom that is inserted into opening 50 and that has a threaded outer surface 120 that mates with a threaded inner surface 122 defining opening 50. Transverse axis stage 46 is configured to move along a transverse axis 116 in both directions 117, 119, which is angled, for example, substantially perpendicularly, relative to primary axis 52. In an embodiment, transverse axis 110, primary axis 52, and the axis along which laser beam 14 travels are substantially orthogonal to each other.

To guide the movement of transverse axis stage 46, a linear bearing stage 124 is coupled to transverse axis stage 46 along a top edge 126 thereof. For example, interior- and outer-facing surfaces 110, 112 adjacent to top edge 126 each includes a groove 128, 130 for containing bearings (not shown) and linear bearing stage 124 includes a channel 132 configured to receive top edge 126 of stage 46 and interior surface 134 with grooves 138, 140 corresponding to grooves 128, 130 for securing bearings (not shown) therebetween. An outer surface 142 of linear bearing 124 is coupled to a T-shaped bracket 144 including a planar stem portion 146 disposed between linear bearing 124 and a transverse axis motor 148 and a perpendicular cap portion 150 along one edge of planar stem portion 146. Cap portion 150 may be disposed alongside a wall of stage housing 152.

Transverse axis motor 148 limits movement of transverse axis stage 46 along transverse axis 116 and is made up of a voice coil motor. Transverse axis motor 148 has a coil 154 and a magnet assembly 156 disposed at least partially within a housing 158. Coil 154 includes a coil holder 160 comprising a base 162 coupled to stem portion 146 of linear bearing 124 and a cylindrical section 164 extending from base 162. An end portion of cylindrical section 164 includes a tubular coil winding 166 wound therearound, which is inserted into a gap 168 formed between a solid cylindrical section 170 and a tubular section 172 surrounding cylindrical section 170 each extending from a cover 174 and making up magnet assembly 156. An inner surface of tubular section 172 includes a magnetic material and is connected to a power source to selectively provide a magnetic field in magnet assembly 156. A remainder of tubular section 172 and surrounding cylindrical section 170 are formed from a soft iron core or other suitable non-magnetizable material.

To determine whether to activate transverse axis motor 148, one or more position sensors (not shown) are coupled to transverse axis stage 46. The position sensors can include an optical, capacitive, inductive, other type of linear encoder or another type of sensor capable of noting exact positioning of transverse axis stage 46 relative to a reference.

Figure 7:
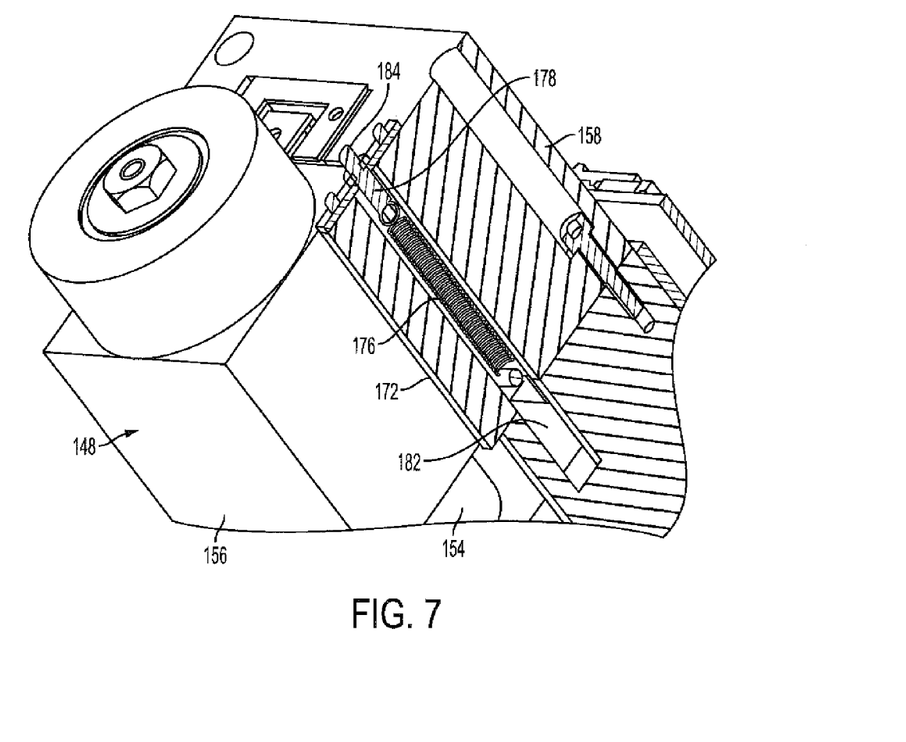
FIG. 7 is a close-up sectional view of a transverse motor housing of the scanning lens of FIG. 2.

A counterbalance spring 176, as illustrated in FIG. 7, selected for a particular spring constant is coupled at one end to magnet assembly 156, such to tubular section 172 and at an opposite end to a pin 178 attached to housing 158. In particular, housing 158 includes a channel 182 formed in one of its walls and pin 178 is disposed in channel 182 such that an exposed head 184 of pin 178 allows one to rotate head 184 to thereby tune positioning of magnet assembly 156 by tightening spring 176 and moving spring 176 axially through channel 182. As a result, magnet assembly 156 moves relative to housing 158.

Figure 3:
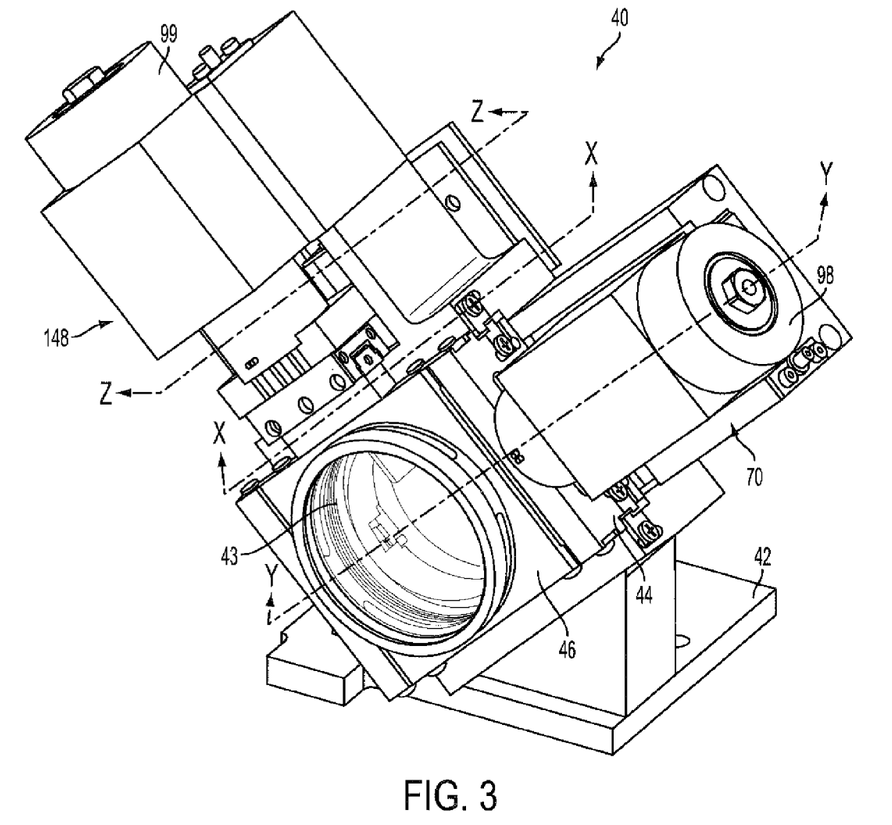
FIG. 3 is a perspective view of a scanning lens component for use in the laser beam delivery system of FIG. 2.

During operation of delivery optics 16, power is supplied to laser 14 to provide laser 14 along the delivery path. In some instances, an external force may be inadvertently transmitted to offset module 38. Typically, the external force is negligible and does not affect movement of offset module 38. However, in an event in which the external force does affect offset module 38, position sensors 94 of primary axis stage 44 and of transverse axis stage 46 feed data to primary and transverse axis motors 70, 148 so that motors 70, 148 can counteract such movement to stabilize both stages 44, 46.

Figure 4:
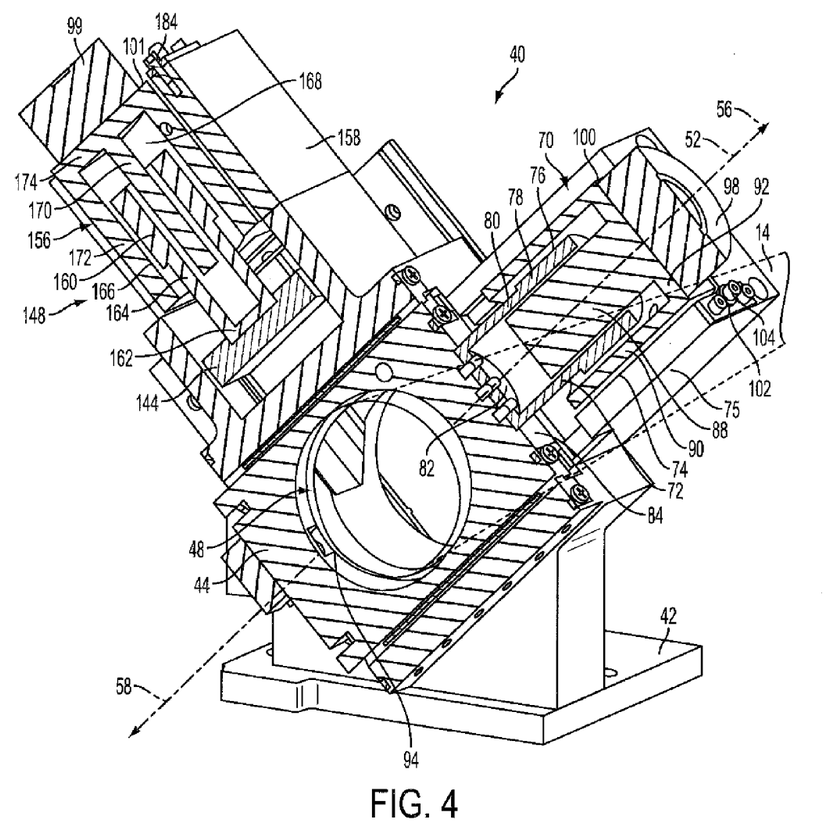
FIG. 4 is a cross section view of the scanning lens component of FIG. 3 taken through a primary axis X-X.

For example, if position sensor 94 detects movement of primary axis stage 44 (and hence, of coil 72) in response to an externally exerted force and the movement is outside of the acceptable range of movement along primary axis 52 in one direction or greater than an allowable predetermined threshold distance along primary axis 52 in that direction, primary axis motor 70 causes magnet assembly 74 to travel along primary axis 52 in an opposite direction. Specifically, the external force exerted on both coil 72 ($F_1$) and magnet assembly 74 ($F_2$) are set as being equal to each other and the mass for each of coil 72 ($m_1$) and magnet assembly 74 ($m_2$) are fixed values. As a result, when coil 72 accelerates along primary axis 52 at an acceleration ($a_1$) in one direction, magnet assembly 74 accelerates along primary axis 52 in an opposite direction at acceleration ($a_2$) such that $m_1 a_1 = m_2 a_2$. In an embodiment, magnet assembly 74 is configured such that when coil 72 travels at $a_1$ along primary axis 52, an appropriate current is provided to magnet assembly 74 to thereby cause magnet assembly 74 to accelerate at $a_2$ along primary axis 52.

Figure 5:
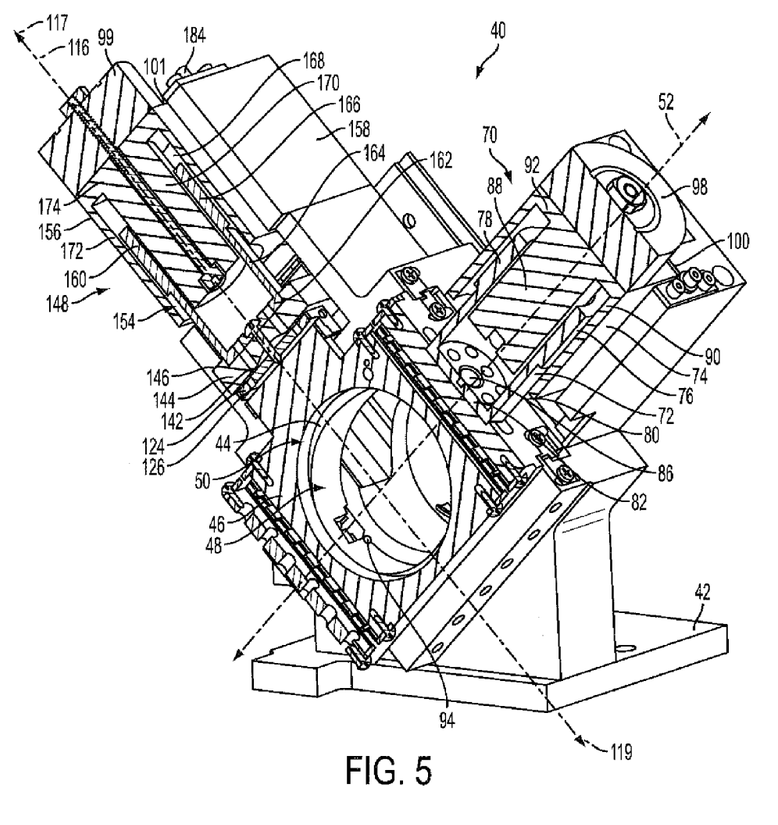
FIG. 5 is a cross section view of the scanning lens component of FIG. 3 taken through a transverse axis Y-Y.
Figure 6:
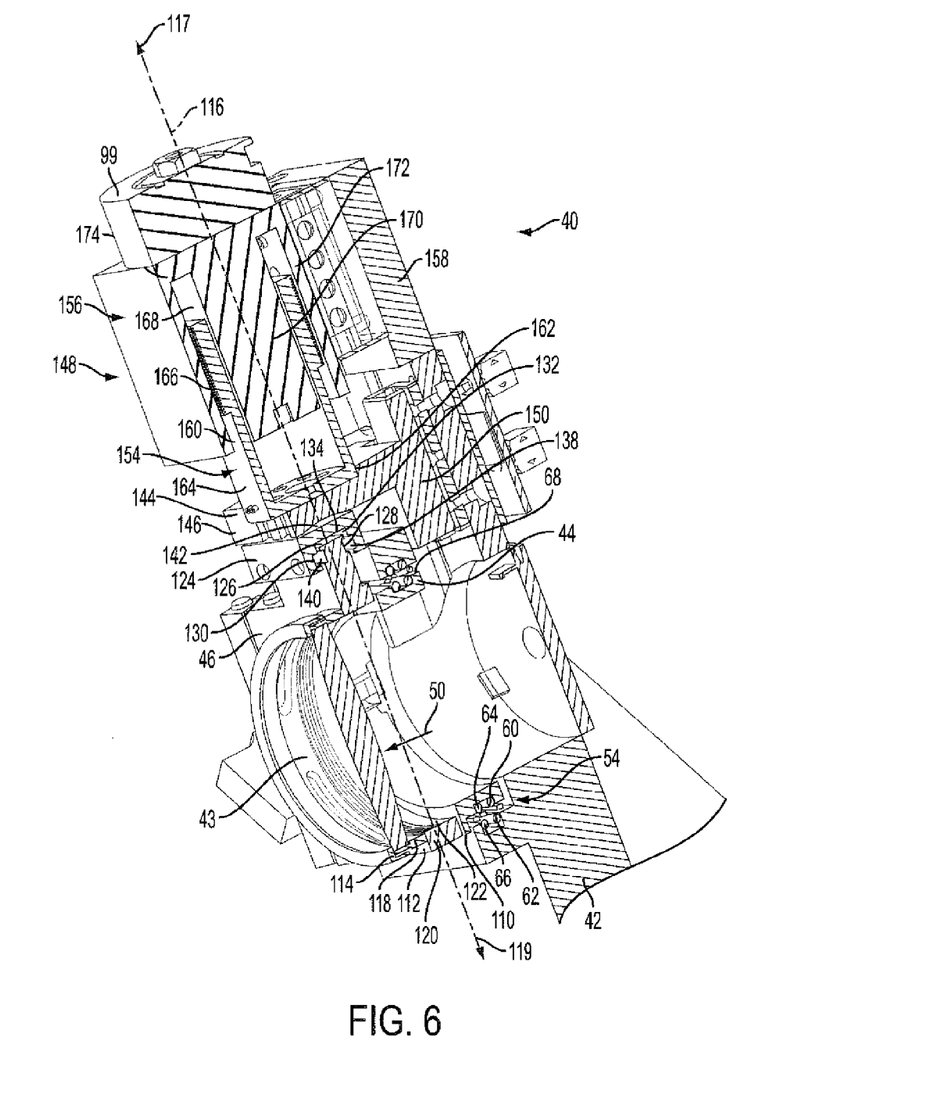
FIG. 6 is a cross section view of the scanning lens component of FIG. 3 taken through a transverse axis Z-Z.

Concurrently, if the position sensor detects movement of transverse axis stage 46 (and hence, of coil 154) in response to an externally exerted force and the movement is outside of the acceptable range of movement allowed along transverse axis 116 or greater than the predetermined threshold distance, transverse axis motor 148 causes magnet assembly 156 to move in an opposite direction along transverse axis 116. In particular, as the external force exerted on both coil 154 ($F_3$) and magnet assembly 156 ($F_4$) are set equal to each other and the mass for each of coil 154 ($m_3$) and magnet assembly 156 ($m_4$) are fixed values, as coil 154 accelerates along transverse axis 116 and magnet assembly 156 accelerates along transverse axis 116 in an opposite direction at respective accelerations ($a_3$), ($a_4$) such that $m_3 a_3 = m_4 a_4$. In an embodiment, magnet assembly 156 is configured such that when coil 154 travels at $a_3$ along transverse axis 116, an appropriate current is provided to magnet assembly 156 to thereby cause magnet assembly 156 to accelerate at $a_4$ along transverse axis 116.

It will be appreciated that the particular values selected for $m_1$-$m_4$ may or may not be equal to each other and may be selected based on space and/or footprint limitations of scanning lens component 40. In some configurations, one mass $m_1$-$m_4$ is greater than another one of the masses $m_1$-$m_4$. For example, to reduce the distance traveled by magnet assembly 74 along primary axis 52 or magnet assembly 156 along transverse axis 116, one or more additional masses 98, 99 can be coupled to cover 92 of primary axis motor 70 or cover 174 of transverse axis motor 148. In one implementation, as shown in FIGS. 3-6, masses 98, 99 are each solid masses attached to covers 92, 174 and extend through an opening 100, 101 in housings 75, 158. Alternatively, one or both masses 98, 99 is omitted.

In any case, by including voice coil motors that include floating magnets and coils to counteract unwanted movement, primary and transverse axis stages 44, 46 remain stationary relative to laser 14 so that laser 14 is directed at lens 43 while no other component interferes with the delivery path. Additionally, by minimizing or eliminating movement of lens 43, and hence insuring that the delivery of laser 14 remains controlled, laser 14 hits minor 30 at a single location through the duration of a laser surgery procedure on the patient.

While at least one exemplary embodiment has been presented in the foregoing detailed description of the inventive subject matter, it should be appreciated that a vast number of variations exist. For example, the scanning lens or lens stage configurations or the beam delivery system of the foregoing exemplary embodiments may be used in conjunction with a variety of laser systems, including diode lasers, $CO_2$ lasers, dye lasers, fiber lasers, gas lasers, optical parametric oscillators, and the like. It should also be appreciated that the exemplary embodiment or exemplary embodiments are only examples, and are not intended to limit the scope, applicability, or configuration of the inventive subject matter in any way. Rather, the foregoing detailed description will provide those skilled in the art with a convenient road map for implementing an exemplary embodiment of the inventive subject matter. It being understood that various changes may be made in the function and arrangement of elements described in an exemplary embodiment without departing from the scope of the inventive subject matter as set forth in the appended claims.

What is claimed is:

1. A scanning lens component of a laser beam delivery system comprising:
   a primary axis stage configured to move linearly along a primary axis in a first direction, the primary axis stage including a first central opening for receiving an incident beam of light;
   a primary axis motor coupled to the primary axis stage and including a first coil and a first magnet, the first coil configured to move along the primary axis in the first direction along with the primary axis stage, and the first magnet configured to move in a second direction opposite the first direction, in response to movement of the first coil along the primary axis in the first direction a first distance that exceeds a threshold primary axis distance;
   a transverse axis stage adjacent and coupled to the primary axis stage, the transverse axis stage including a second central opening substantially aligned with the first central opening and being configured to move at least linearly along a transverse axis in a third direction, the transverse axis being transverse relative to the primary axis; and
   a transverse axis motor coupled to the transverse axis stage and including a second coil and a second magnet, the second coil configured to move along the transverse axis in the third direction along with the transverse axis stage, and the second magnet configured to move in a fourth direction opposite the third direction, in response to movement of the second coil along the transverse axis in the third direction a second distance that exceeds a threshold transverse axis distance.

2. The scanning lens component of claim 1, further comprising:
a first linear bearing coupled between the primary axis stage and the first coil and substantially aligned with the primary axis.

3. The scanning lens component of claim 2, further comprising:
a second linear bearing coupled between the transverse axis stage and the second coil and substantially aligned with the transverse axis.

4. The scanning lens component of claim 3, further comprising:
a third linear bearing coupled to the second magnet configured to receive a portion of the second coil.

5. The scanning lens component of claim 4, further comprising:
a primary axis motor housing within which the first magnet is at least partially disposed;
a counterbalance spring coupled to the primary axis motor housing and the first magnet, the counterbalance spring configured to suspend the first magnet at a desired position relative to the first coil.

6. The scanning lens component of claim 4, further comprising:
a transverse axis motor housing within which the second magnet is at least partially disposed;
a counterbalance spring coupled to the transverse axis motor housing and the second magnet, the counterbalance spring configured to suspend the second magnet at a desired position relative to the second coil.

7. The scanning lens component of claim 1, further comprising a lens disposed along the primary axis and coupled to the transverse axis stage.

8. The scanning lens component of claim 7, further comprising a pinhole alignment plate disposed adjacent to the primary axis stage and configured to align with the first central opening thereof.

9. The scanning lens component of claim 1, further comprising a first position sensor coupled to the primary axis stage configured to detect a position thereof.

10. The scanning lens component of claim 9, further comprising a second position sensor coupled to the transverse axis stage configured to detect a position thereof.

11. The scanning lens component of claim 1, wherein the primary axis and the transverse axis are substantially perpendicular.

12. The scanning lens component of claim 1, wherein the primary axis motor and the transverse axis motors each comprise a voice coil motor.

13. A method of reducing reaction forces in a scanning lens apparatus, the method comprising:
detecting a change in positioning of a primary axis stage in a first direction coupled to a first coil of a primary axis motor, each movable along a primary axis in the first direction and in an opposite second direction;
determining whether the change in the positioning of the primary axis stage along the primary axis exceeds a threshold value;
moving a first magnet surrounding at least a portion of the first coil in the second direction along the primary axis, in response to the change in the positioning of the primary axis stage in the first direction, if the change exceeds the threshold value;
detecting a change in positioning of a transverse axis stage in a third direction coupled to a second coil of a transverse axis motor, each movable along a transverse axis that is substantially perpendicular to the primary axis in the third direction and in a fourth direction opposite the third direction, and the transverse axis stage disposed adjacent and coupled to the primary axis stage;
determining whether the change in the positioning of the transverse axis stage exceeds a threshold value; and
moving the second magnet surrounding at least a portion of the second coil in the fourth direction along the transverse axis, in response to the change in the positioning of the transverse axis stage in the third direction, if the change exceeds the threshold value.

14. The method of claim 13, further comprising adjusting a counterbalance spring coupled between the first magnet of the primary axis motor and a primary axis housing to a maintain the first magnet in an initial neutral position, prior to the step of detecting a change in positioning of a primary axis stage in a first direction.

15. The method of claim 14, further comprising adjusting a counterbalance spring coupled between the second magnet of the transverse axis motor and a transverse axis housing to a maintain the second magnet in an initial neutral position, prior to the step of detecting a change in positioning of a transverse axis stage in a third direction.

16. A scanning lens system comprising:
a primary axis stage including a first central opening for receiving an incident beam of light, the primary axis stage movable along a primary axis in a first direction and in an opposite second direction;
a transverse axis stage disposed adjacent to the primary axis stage and including a second central opening for receiving the incident beam of light, the transverse axis stage movable along a transverse axis in a third direction and in an opposite fourth direction, and the transverse axis being substantially orthogonal to the primary axis;
a lens coupled to the transverse axis stage;
a primary axis voice coil motor coupled to the primary axis stage and including a first coil movable with the primary axis stage and a first magnet configured to move along the primary axis in the second direction, if the primary axis stage moves a distance along the primary axis in the first direction that exceeds a first predetermined threshold value; and
a transverse axis voice coil motor coupled to the transverse axis stage including a second coil movable with the transverse axis stage and a second magnet configured to move along the transverse axis in the fourth direction, if the transverse axis stage moves a distance along the transverse axis in the third direction that exceeds a second predetermined threshold value.

17. The scanning lens system of claim 16, further comprising:
a first linear bearing coupled between the primary axis stage and the first coil and aligned with the primary axis stage, the first linear bearing configured to guide the primary axis stage and the first coil along the primary axis; and
a second linear bearing coupled between the transverse axis stage and the second coil and aligned with the transverse axis stage, the second linear bearing configured to guide the transverse axis stage and the second coil along the transverse axis.

18. The scanning lens system of claim 17, further comprising a support bracket coupled between the second linear bearing and the second coil of the transverse axis motor.

19. The scanning lens system of claim 17, further comprising a third linear bearing coupled to the second magnet configured to guide the second magnet along the transverse axis.

20. The scanning lens system of claim 16, further comprising:
- a first housing including a cavity within which the first magnet is at least partially disposed; and
- a first counterbalance spring including a first end attached to the first housing and a second end attached to the first stationary magnet configured to be adjustable to move the first magnet to a predetermined initial position.

21. The scanning lens system of claim 16, further comprising:
- a second housing including a cavity within which the second magnet is at least partially disposed; and
- a second counterbalance spring including a first end attached to the second housing and a second end attached to the second magnet configured to be adjustable to move the second magnet to a predetermined initial position.

22. The system of claim 16, further comprising:
- a first position sensor coupled to the primary axis stage configured to sense positioning of the primary axis stage along the primary axis; and
- a second position sensor coupled to the transverse axis stage configured to sense positioning of the transverse axis stage along the transverse axis;

wherein:
- the positioning sensed by the first position sensor and the second position sensor are provided to the primary axis motor and the transverse axis motor, respectively.

* * * * *